(12) United States Patent
Burgard

(10) Patent No.: US 7,485,087 B2
(45) Date of Patent: Feb. 3, 2009

(54) FISTULA BLOCKER

(76) Inventor: Gunther Burgard, Fasanenweg 7, Homburg (DE) 66424

( * ) Notice: Subject to any disclaimer, the term of this patent is extended or adjusted under 35 U.S.C. 154(b) by 753 days.

(21) Appl. No.: 10/911,958

(22) Filed: Aug. 5, 2004

(65) Prior Publication Data

US 2005/0049626 A1    Mar. 3, 2005

Related U.S. Application Data

(63) Continuation of application No. 10/009,242, filed as application No. PCT/EP00/05273 on Jun. 7, 2000, now abandoned.

(30) Foreign Application Priority Data

Jun. 7, 1999    (DE)    ............................ 299 09 888 U

(51) Int. Cl.
     *A61F 2/02*    (2006.01)
(52) U.S. Cl. ........................................................ 600/32
(58) Field of Classification Search ................. 606/151, 606/153, 213, 214, 215, 216; 600/30, 31, 600/32; 128/DIG. 25
See application file for complete search history.

(56) References Cited

U.S. PATENT DOCUMENTS

| | | | |
|---|---|---|---|
| 2,898,913 | A | 8/1959 | Ritter et al. |
| 3,648,683 | A | 3/1972 | Brodie |
| 3,949,750 | A | 4/1976 | Freeman |
| 4,209,009 | A * | 6/1980 | Hennig .................. 600/30 |
| 4,890,612 | A | 1/1990 | Kensey |
| 4,981,465 | A * | 1/1991 | Ballan et al. .................. 600/32 |
| 5,053,046 | A | 10/1991 | Janese ........................ 606/215 |
| 5,374,261 | A | 12/1994 | Yoon ....................... 604/385.1 |
| 5,549,122 | A * | 8/1996 | Detweilwer ................. 606/151 |
| 6,569,081 | B1 * | 5/2003 | Nielsen et al. ................. 600/32 |

FOREIGN PATENT DOCUMENTS

| | | |
|---|---|---|
| DE | 2 132 122 | 2/1972 |
| DE | 2 637 119 A1 | 3/1977 |
| DE | 26 37 119 A1 | 3/1977 |
| DE | 27 22 286 A1 | 11/1978 |
| DE | 41 01 937 A1 | 7/1992 |
| EP | 0 894 474 A1 | 2/1999 |
| FR | 2 625 897 | 7/1989 |
| SU | 1204193 A | 1/1986 |
| SU | 1718837 A1 | 3/1992 |
| WO | WO 89/11301 | 11/1989 |
| WO | WO 94/28800 | 12/1994 |
| WO | WO 96/04954 A1 | 2/1996 |
| WO | WO 98/06344 | 2/1998 |

* cited by examiner

*Primary Examiner*—Kevin T Truong
(74) *Attorney, Agent, or Firm*—Seed IP Law Group PLLC; Hai Han

(57) ABSTRACT

In order to create a treatment device for clearing up fistulas with which fistulas can be treated as sparingly as possible, and where the functions of the adjacent anatomical structures are to remain as intact as possible, the invention proposes a fistula blocker for clearing up a fistula passage with a plug-like closure device, at least somewhat insertable into a fistula passage, which has a bearing surface which extends at least in part circumferentially transverse to the direction of insertion and which can be brought into contact with the wall of a fistula passage, and where the closure device is provided with flexible application string which can be inserted into the fistula passage, the latter being designed as a drainage pipe.

52 Claims, 3 Drawing Sheets ns after vessel operations, particularly in blood vessels. The closure device is inserted into the blood vessel with the aid of a sleeve which for example has already been used for a catheter, and is pulled through the passage from inside. For pulling it in a thread is available which is pulled outwards and fastened and whose material decomposes after a certain period of time in the body.

FISTULA BLOCKER

CROSS-REFERENCE TO RELATED APPLICATIONS

This application is a continuation of U.S. patent application Ser. No. 10/009,242, filed Apr. 3, 2002 (now pending); which application is a U.S. National Phase Application of International Application No. PCT/EP00/05273, filed Jun. 7, 2000; which claims priority to German Patent Application No. 299 09 888.5, filed Jun. 7, 1999; all of which applications are incorporated herein by reference in their entireties.

BACKGROUND OF THE INVENTION

1. Field of the Invention

The invention refers to a fistula blocker to clear up a fistula passage, in particular for treatment of anal, bladder, intestinal and urogenital fistulas.

2. Description of Related Art

Fistulas are tubular shaped tissue-lined connectors between body cavities or hollow organs amongst themselves or to the surface of the body. They frequently develop as a consequence of infections or accompany abscess formation. For example, anal fistulas arise primarily from an infection of the so-called proctodeal gland. Anal fistulas generally form a connection between the end of the large intestine (rectum) and the outside skin of the buttocks. In doing so, they frequently riddle the sphincter.

In the conventional manner, the majority of anal fistulas are treated with the so-called "lay open" technique. Here the fistula is carefully probed and the tissue lying above it is transected, normally with the sphincter (closing) muscles. Transecting is carried out until the bottom of the separation point is formed by the longitudinally split passage of the fistula. This separation point heals upward from below so that the fistula closes. Due to transecting of the sphincter muscles, however, there is a danger of subsequent incontinence of the patient.

SU 1 718 837 A1 described a method for treating large intestinal fistulas which for example connect the large intestine with the abdominal wall. Here a wire is introduced from the outside up through the inner opening of the fistula. An obturator is guided with the aid of an endoscope through the large intestine to the inner opening. The obturator is attached to the end of the wire and is pulled into the inner opening of the fistula canal so that it closes. Subsequently the wire is removed and the outer opening is closed off with the aid of a separate obturation section. In this way, the fistula path passage is eliminated.

SU 1 204 193 A disclosed an obturator for closing off bronchio-pleural fistulas after pneumectomy treatment. The obturator has a truncated cone shape with an opening at the end of the obverse side. A bulb-headed probe is introduced into the opening on the obverse side with the aid of which the obturator is introduced into the fistula opening after its surface and the walls of the fistula have been provided with medical glue. With the aid of the glue, the obturator is fastened to the wall of the fistula and the bulb-headed probe is subsequently removed again.

DE 26 37 119 A1 proposes an inflatable balloon as a closure device for closing off blood vessels or fistulas after surgical intervention, it being possible to guide the balloon into the vessel in question, to inflate it and to leave it there. After positioning and inflating the balloon, a hose pipe is separated from the balloon for inflating the latter and pulled out of the body.

The Publication WO89/11301 describes a somewhat sponge-like closure device for closing off punctures or incisions after vessel operations, particularly in blood vessels. The closure device is inserted into the blood vessel with the aid of a sleeve which for example has already been used for a catheter, and is pulled through the passage from inside. For pulling it in a thread is available which is pulled outwards and fastened and whose material decomposes after a certain period of time in the body.

BRIEF SUMMARY OF THE INVENTION

The object of the invention is to create a treatment device for clearing up fistulas with which fistulas can be treated as sparingly as possible and where the functions of the adjacent anatomical structures remain as intact as possible.

This object is achieved according to the present invention with a fistula blocker for clearing up a fistula passage with a plug-like closure device which can be at least partially inserted into the fistula passage, and which has a bearing surface which at least to some extent along its circumference can be brought into contact with the wall of a fistula passage transverse to the direction of insertion, and in which case the closure device is provided with a flexible application string insertable into the fistula passage, the application string being formed as a drainage pipe.

This fistula blocker makes possible a substantial improvement of operating techniques. After the fistula has been probed, the fistula blocker can be inserted into the opening of the fistula passage and positioned as deeply as required. With the aid of the closure device the fistula passage is closed off as much as possible on one side so that pathogens are blocked off by the closure device on this side. The bearing surface of the closure device is located in inserted condition in contact with the wall of the fistula passage resulting in a certain sealing effect.

The application string can be inserted into the fistula and optionally can pull the closure device with it into the fistula passage. By being designed as a drainage pipe the application string can at least for a while remain in the fistula. Secretions or pus liquids can be evacuated from the fistula passage via the drainage pipe so that inflammation hotbeds can be removed to the outside. As a drainage pipe, for instance, one can imagine a drainage thread on which germinating secretions can be led outside from the fistula passage by means of its wick-like action.

The fistula blocker according to this invention makes possible an extremely gentle treatment of the fistula, in particular for adjacent tissue. While according to state-of-the-art techniques, adjacent tissue up to the bottom of the fistula passage was severed, with the fistula blocker a gentle treatment technique is possible which is essentially better tolerated by patients and which hardly impacts on the adjacent anatomical structures.

Preferentially, the closure device can have a guide section located cranially in the direction of insertion. The guide section facilitates insertion of the closure device, in which case it aligns the closure device according to the anatomical trajectory of the fistula passage.

Particularly usefully, the closure device can have a closure section having the bearing surface located caudally in the direction of insertion. With the aid of the closure section, the fistula passage can be blocked. The closure section is preferably located with the bearing surface on the walls of the fistula passage.

More appropriately, the closure device can be formed tapering off conically in the cranial direction. The conical shape makes it easier to insert the closure device with the tapering-off guide end. When the closure device is pushed forward, the fistula passage is slightly spread out, thus the fistula passage is folded out and the closure device with the aid of the bearing surface touches fairly tightly to the fistula's wall.

As a variant of the invention, the closure device can be shaped conically. The conical shape entails a continuously expanding outer diameter of the closure device, so that when inserted in the fistula passage up to the required depth it can be pushed into the fistula opening up to the diameter corresponding to that of the fistula passage.

The closure device may possibly have a concave outer shape. This is particularly good with a concave expanding cross-section shape of the closure device tending towards the caudal direction, and in the range of which the bearing surface should preferably be laid out, so that that surface can be inserted particularly easily into the fistula opening or attaches itself on the outside to the surroundings of the fistula opening until the fistula passage is blocked.

As a variant of the invention, the closure device can be shaped like an egg.

It is feasible to have the closure device shaped rotationally symmetric to its longitudinal axis, In accordance with a preferred embodiment, the length of the closure device in the direction of insertion can correspond to about 2 cm, preferably 0.5 to 1 cm. With this length, a fistula passage can be effectively blocked. The bearing surface can be shaped sufficiently long in the direction of insertion in order to effectively block the fistula. A closure device of this length can be worn by a patient for a protracted period of time without any problems.

The closure device can preferably be made of absorbable material. In this way, the closure device's material can be broken down over a specific period of time. While the closure device at first blocks the fistula, it is slowly converted by the body in the course of time and ultimately, depending on the type of material, even completely dissolved.

Particularly advantageous is making the closure device out of poly-dioxanone, poly-glycolic acid and/or trimethyl carbonate. These materials can be reabsorbed in the long run and can be slowly broken down by the body itself and absorbed.

It is particularly advantageous to make the closure device of metal, preferably titanium.

Particularly advantageous is to have the closure device hollowed out on the inside. In this way, relatively little foreign matter is inserted into the fistula passage. If the hollow structure on the inside of the closure device is accessible from outside, then the closure device can be riddled with the body's own tissue, something that promotes granulation with absorbable material.

It is proposed that the closure device have a semi-permeable porous surface structure running from cranial to caudal, preferably as membrane. In this way, substances such as pus and liquid can be led off from the fistula passage through the closure device from cranial to caudal while the penetration of impurities from the outside can be prevented.

The closure device can possibly have a spongy structure. This facilitates absorption and granulation of the closure device. With a spongy surface structure of the closure device, the body's own substances can easily penetrate the closure device and convert the latter or decompose it over a longer period of time.

As a variant of the invention, the closure device can be permeated with channels on the inside. This facilitates absorption of the closure device.

Advantageously, the closure device should have several indentations spread out over its surface. The indentations increase the grip of the closure device so that the latter is more firmly attached to the wall of the fistula passage. The indentations, e.g. in the form of dimples, furthermore promote absorption.

In accordance with a special embodiment, the fistula blocker can be provided with an anchoring device which holds the closure device tight in a fistula passage. In this way, the fistula blocker in the body can be securely fastened even if the patient moves.

It is possible to have the anchoring device have one or more barbed sections blocking movement in the direction opposite that of insertion. With the barbed sections, movement opposite the direction of insertion is inhibited so that the anchoring device cannot inadvertently slip out of the fistula.

In a special way, the barbed sections can be flexible to a limited extent, laid out to the side of the fistula blocker shoring up itself. In this way, the barbed sections themselves protrude and inhibit any independent movement of the fistula blocker contrary to the direction of insertion.

In order to select a fistula blocker based on this invention appropriate to the size and anatomy of the fistula passage to be treated and to achieve tight fit of the fistula blocker, according to this invention separate fistula blocker stencils can be used. Such fistula blocker stencils for insertion in a fistula passage have a plug-like closure device, insertable at least to some extent in the fistula passage which has a bearing surface which can to at least some extent be placed circumferentially perpendicular to the direction of insertion and in contact with the wall of the fistula passage. Such fistula stencils can be made available in different sizes and shapes so that successively several different closure devices can be tried out on the patient and accordingly a fistula blocker of appropriate size and shape can be selected and ultimately deployed.

The fistula blocker stencils may preferably show a closure device having the previously mentioned specific features of the fistula blocker's closure device.

Embodiment examples of the invention are illustrated in the drawings and are explained below.

DETAILED DESCRIPTION OF THE INVENTION

Figures 1, 2, 3:
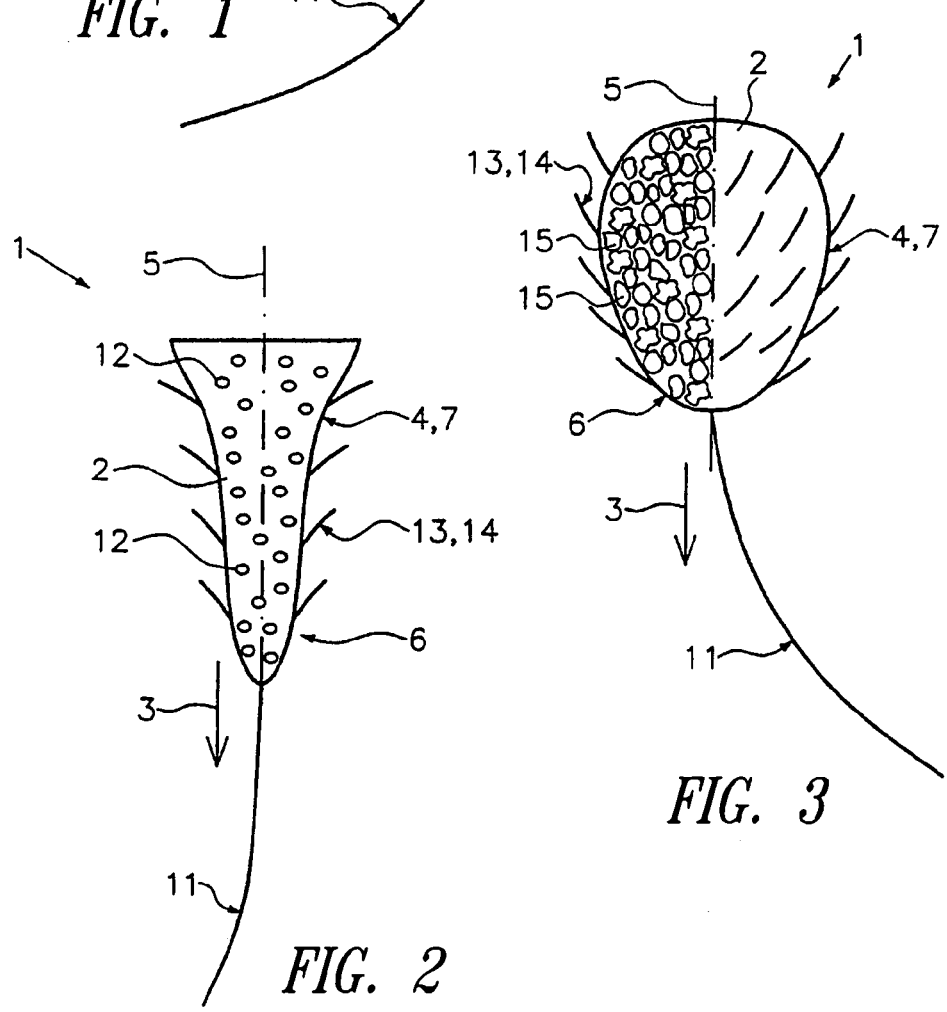
FIG. 1 shows a side view of a fistula blocker according to this invention according to the first embodiment.
FIG. 2 shows an enlarged side view of a fistula blocker according to this invention according to a second embodiment.
FIG. 3 shows an enlarged side view of a fistula blocker according to this invention according to a third embodiment.

In FIG. 1, a first embodiment of a fistula blocker 1 according to this invention for sanifying a fistula passage is shown. The fistula blocker has a plug-like closure device 2 which can be inserted into a fistula passage in the direction of insertion 3. The closure body 2 has a conical shape with a caudal thick end and a cranial thin end. The caudal end refers in this sense to the end contrary to the direction of insertion 3 while the cranial end is the end of the closure device 2 pointing in the direction of insertion 3.

The closure device 2 has a bearing surface 4 extending transverse to the direction of insertion 3 which is given with the conical shape by the surface of the cone's envelope. This surface is at least in places in contact with the wall of a fistula passage. The conical shape is rotationally symmetric to the longitudinal axis 5 of the closure device 2.

The cranial end of the closure device forms a guide section 6 and the caudal end of the closure device 2 forms a closing section 7 containing the bearing surface 4 and, when the fistula blocker 1 is inserted, is in contact with the wall of the fistula passage.

The outside surface of the closure device has several dimple-like indentations 8. The closure device 2 has on the inside an approximately conically shaped hollow space 9 which is closed off at the end by a wall 10.

At its conically pointed cranial end, the closure device 2 is connected to an application string 11 which is flexible and can be inserted into a fistula passage. The application string is formed as a drainage thread so that it can serve to evacuate liquids out of the fistula. The application string can have a length of about 20 cm.

The closure device 2 has on the outside a semi-permeable surface structure porous in the direction from cranial to caudal and impenetrable in the opposite direction. Its surface can have a corresponding membrane or the entire closure device 2 can be formed like a membrane.

In FIG. 2, a second invention embodiment of a fistula blocker 1 is shown. Identical reference symbols designate identical elements so that in this regard reference can be made to the details above unless the following description provides an explanation diverging from it.

The closure device of the fistula blocker 1 according to the second embodiment has a closure section 7 with a concave outer shape expanding outward caudally. With the outer bearing surface 4 the fistula blocker 1 can get into contact with the fistula passage. The cranial guide section 6 of the closure device 2 has a shape which is arched somewhat convex forward and inwardly and which leads to the application string 11. In this way, the closure device 2 has somewhat of a bell shape longitudinally.

The closure device 2 is riddled on the inside with channels which via the channel openings 12 border on the outer surface of the closure device 2.

The closure device 2 is provided with an anchoring device 13 which has several barbed sections 14 distributed longitudinally to the girth and length of the closure device 2. The barbed sections 14 branch off laterally shored up from the closure device 2 and are aligned somewhat contrary to the direction of insertion 3. They are flexible to a limited extent.

In FIG. 3 a third embodiment of a fistula blocker 1 according to the invention is shown. Identical reference symbols designate identical sections as in the details above so that in this regard reference can be made to the description above, unless something diverging from that is said below.

The closure device 2 has a somewhat egg-like shape the slimmer end of which is pointed in the direction of insertion 3. The closure device 2 has a spongy hollow structure which is illustrated in cross-section in the left half of the closure device 2. The spongy structure is shown in the form of several pores 15 which extend up to the outer surface of the closure device 2. The surface of the closure device 2 likewise has a correspondingly spongy structure. Accordingly, the closure device has a porous hollow structure inside.

In the right half, the closure device 2 is shown from the outside where for reasons of visibility the spongy structure has been deleted. On the outer side, the closure device 2 likewise has a corresponding anchoring device 13 with barbed sections 14.

The fistula blockers 1 of the first to third embodiments have a closure device 2 with a length of about 2 cm, preferably 0.5 to 1 cm, measured in the direction of insertion. They may be made out of absorbable material like poly-dioxanone, poly-glycolic acid and/or trimethyl-carbonate.

The closure device can likewise be made out of non-absorbable material like metal, preferably titanium.

Figure 4:
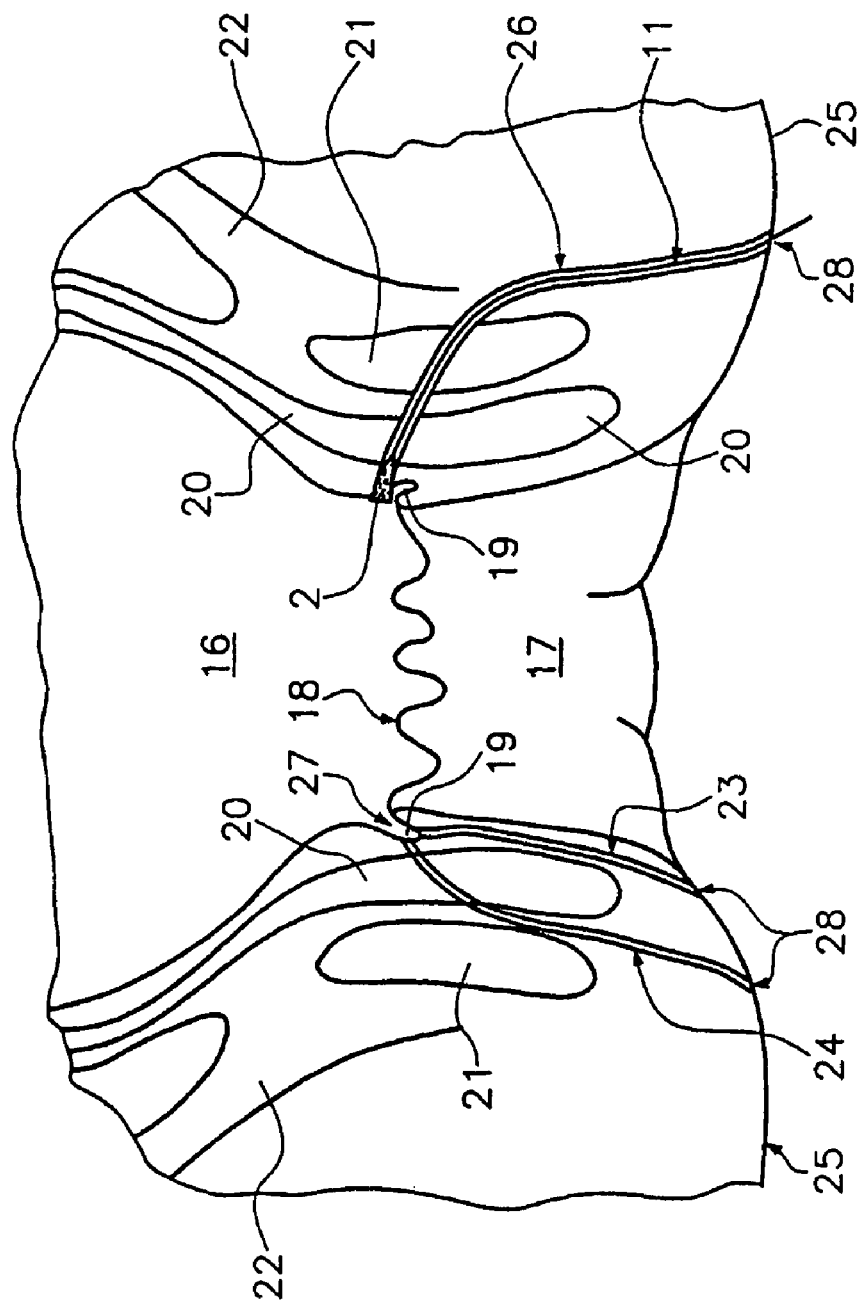
FIG. 4 shows a longitudinal section through a human rectum with adjacent anatomical structures and a fistula blocker according to this invention inserted.

In FIG. 4 a longitudinal section through the rectum of a human being is shown with adjacent anatomical structures. The anal canal 17 connects to the rectum 16 where between the two there extends the linea dentata 18. At the transition from rectum to the anal canal, there is in the wall the proctodeal gland in the vicinity of which fistula passages increasingly form. Furthermore; in accordance with the anatomical peculiarities there is an inner closure muscle 20, an external closing muscle 21 and a musculus levator ani 22 depicted.

In the left half as examples two fistula passages 23 and 24 are shown which in both cases proceed from the area of the proctodeal gland 19 and extend up to the outside skin of one of the buttocks 25. While the fistula passage 23 runs subcutaneously, the fistula passage 24 extends through the inside closure muscle 20.

In the right half a fistula passage 26 is shown which extends through the inner and external closure muscle 20 and 21, in other words in a so-called trans-sphincter trajectory. All fistula passages have an inner opening 27 proceeding from the rectum 16 and one outer opening 28 located on the outside buttocks 25.

A fistula blocker 1 has been drawn into the fistula passage 26, The closure body 2 sits tightly in the area of the inner opening 27 where its bearing surface 4 is in close contact with the wall of the fistula passage 26.

The application string 11 extends from the guide section 6 of the closure device 2 through the fistula passage 26 up to and through the outside opening 28 and protrudes outward from there.

Figure 5:
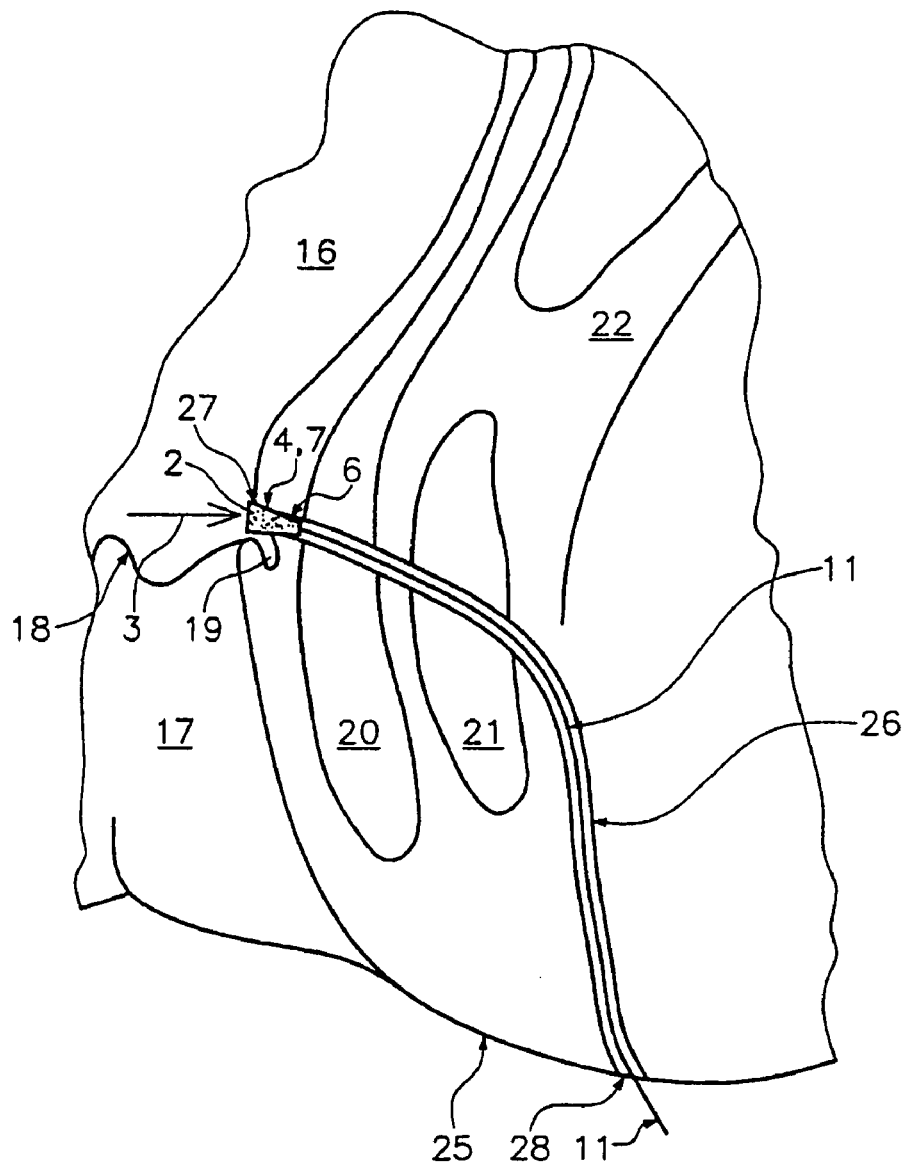
FIG. 5 shows an enlarged presentation of the right part of FIG. 4 with a fistula blocker according to this invention inserted.

In FIG. 5 an enlarged illustration of the right portion of FIG. 4 is shown.

Identical reference symbols designate identical sections so that in this regard reference can be made to the details above.

In FIG. 5 the caudal end of the closure device 2 extends somewhat into the rectum 16. This end can be severed off after insertion of the closure device 2, e.g. with an appropriate forceps so that the closure device 2 ends flush with the inside wall of the rectum 16. The closure device 2 corresponds to the first embodiment illustrated in FIG. 1.

The application string 11 extends over the entire length of the fistula passage up until the outside opening 28 and protrudes out of the latter for about 1-2 cm.

Below, the methods of impacting and functioning of the embodiments of a fistula blocker according to this invention shown in the drawing are explained in greater detail.

A fistula is first of all probed, in other words an appropriate rod-like instrument is pushed into the fistula passage from the outside opening 28 and the fistula's trajectory is investigated. This instrument is pushed forward until it protrudes from the inner opening 27. Subsequently, the application string is pulled through the fistula passage 26 from the inside opening 27 up to the outside opening 28 until the closure device sticks in the inner opening 27 and the guide section 6 opens into the fistula passage. The closure device 2 is pushed as far as necessary for it to sit tightly in the fistula passage 26. A caudal end protruding into the rectum 16 can optionally be severed off. The application string 11 extends several centimeters outwards from the outer opening 28.

The closure device 2 closes off the inner opening 27 so that no contamination of the fistula passage can occur from inside. The barbed sections 14 arrest the movement of the closure device so that it does not inadvertently slip into the rectum 16.

The closure device 2 forms a thick closure. It can be made of semi-permeable material so that secretion from the fistula passage can penetrate through it as far as into the rectum.

It is also possible to have the closure section 7 applied so as to insulate on the inner wall of the rectum above the inner opening 27, in other words adjoining the fistula passage on the outside.

The application string serves as a drainage pipe. It is designed as a thread along which secretions, e.g. pus, due to the wick action of the thread are led off to the outside through the outer opening 28. In this way, substances forming germs are led off from the fistula passage so that the latter can heal by itself. The application string can be absorbable.

Where the closure device 2 is made of absorbable material it can be reabsorbed by the body over a protracted period of time, about 6-12 weeks. This is particularly speeded up if it has a porous spongy surface structure so that it can be slowly converted from the inside by the body's own substances.

Where the closure device 2 is not made out of absorbable material it can remain in the fistula passage for a protracted period of time.

Depending on the anatomic peculiarities of the fistula passage, the closure device 2 can also be inserted deeper into the fistula passage than is shown in FIG. 5.

The size fitting the fistula opening of the closure device 2 can, for instance, be determined by separate test-fit stencils. These test-fit stencils correspond to the shapes of the closure device 2, as described for the three embodiments, in applicable cases without barbed sections 14. Several stencils of differing sizes are available so that the precise fit is determined for each particular fistula and accordingly a fistula blocker 1 can be selected with a closure device 2 of appropriate size.

The fistula blocker constituting the invention makes possible extremely gentle treatment of a fistula where the invasive intervention of traditional treatments is substantially reduced so that tissue are hardly injured and the patient experiences an extremely gentle treatment of the fistula.

What is claimed is:

1. A fistula blocker, for clearing up a fistula passage comprising:
    a plug-like closure device comprising a bearing surface, a caudal end and a cranial end, the bearing surface extending at least partially circumferentially and transverse to the direction of insertion and being in contact with the interior wall of the fistula passage when the device is inserted into the fistula passage, wherein the plug-like closure device has a semi-permeable surface; and
    a flexible application string directly attached to the cranial end of the plug-like closure device, the application string providing drainage of liquids out of the fistula passage.

2. The fistula blocker of claim 1, wherein the cranial end of the plug-like closure device comprises a guide section.

3. The fistula blocker of claim 1, wherein the caudal end of the plug-like closure device comprises a closure section.

4. The fistula blocker of claim 1, wherein the plug-like closure device has a conical shape.

5. The fistula blocker of claim 1, wherein the plug-like closure device has a concave outer shape.

6. The fistula blocker of claim 1, wherein the plug-like closure device has an egg shape.

7. The fistula blocker of claim 1, wherein the length of the plug-like closure device is about 2 cm.

8. The fistula blocker of claim 1, wherein the plug-like closure device comprises an absorbable material.

9. The fistula blocker of claim 1, wherein the plug-like closure device comprises one or more of poly-dioxanone, poly-glycolic acid and trimethyl-carbonate.

10. The fistula blocker of claim 1, wherein the plug-like closure device comprises metal.

11. The fistula blocker of claim 1, wherein the plug-like closure device is hollow.

12. The fistula blocker of claim 1, wherein the plug-like closure device has a spongy structure.

13. The fistula blocker of claim 1, wherein the plug-like closure device comprises a plurality of channels disposed therein.

14. The fistula blocker of claim 1, wherein the plug-like closure device comprises a plurality of indentations on the surface thereof.

15. The fistula blocker of claim 1, wherein the plug-like closure device further comprises an anchoring device.

16. The fistula blocker of claim 15, wherein the anchoring device comprises a plurality of barbed sections.

17. The fistula blocker of claim 16, wherein the plurality of barbed sections are restricted in their flexibility.

18. The fistula blocker of claim 1, wherein the length of the plug-like closure device is 0.5 to 1 cm.

19. The fistula blocker of claim 10, wherein the plug-like closure device comprises titanium.

20. A fistula blocker, for clearing up a fistula passage comprising:
    a plug-like closure device comprising a bearing surface, a caudal end and a cranial end, the bearing surface extending at least partially circumferentially and transverse to the direction of insertion and being in contact with the interior wall of the fistula passage when the device is inserted into the fistula passage, wherein the plug-like device includes a plurality of barbed sections;
    a flexible application string directly attached to the cranial end of the plug-like closure device, the application string providing drainage of liquids out of the fistula passage.

21. The fistula blocker of claim 20, wherein the cranial end of the plug-like closure device comprises a guide section.

22. The fistula blocker of claim 20, wherein the caudal end of the plug-like closure device comprises a closure section.

23. The fistula blocker of claim 20, wherein the plug-like closure device has a conical shape.

24. The fistula blocker of claim 20, wherein the plug-like closure device has a concave outer shape.

25. The fistula blocker of claim 20, wherein the plug-like closure device has an egg shape.

26. The fistula blocker of claim 20, wherein the length of the plug-like closure device is about 2 cm.

27. The fistula blocker of claim 20, wherein the plug-like closure device comprises an absorbable material.

28. The fistula blocker of claim 20, wherein the plug-like closure device comprises one or more of poly-dioxanone, poly-glycolic acid and trimethyl-carbonate.

29. The fistula blocker of claim 20, wherein the plug-like closure device comprises metal.

30. The fistula blocker of claim 20, wherein the plug-like closure device is hollow.

31. The fistula blocker of claim 20, wherein the plug-like closure device has a semi-permeable surface.

32. The fistula blocker of claim 20, wherein the plug-like closure device has a spongy structure.

33. The fistula blocker of claim 20, wherein the plug-like closure device comprises a plurality of channels disposed therein.

34. The fistula blocker of claim 20, wherein the plug-like closure device comprises a plurality of indentations on the surface thereof.

35. The fistula blocker of claim 20, wherein the plurality of barbed sections are restricted in their flexibility.

36. The fistula blocker of claim 20, wherein the length of the plug-like closure device is 0.5 to 1 cm.

37. The fistula blocker of claim 29, wherein the plug-like closure device comprises titanium.

38. A fistula blocker, for clearing up a fistula passage comprising:
   a plug-like closure device comprising a bearing surface, a caudal end and a cranial end, the bearing surface extending at least partially circumferentially and transverse to the direction of insertion and being in contact with the interior wall of the fistula passage when the device is inserted into the fistula passage, wherein the plug-like closure device is formed of metal, and
   a flexible application string directly attached to the cranial end of the plug-like closure device, the application string providing drainage of liquids out of the fistula passage.

39. The fistula blocker of claim 38, wherein the cranial end of the plug-like closure device comprises a guide section.

40. The fistula blocker of claim 38, wherein the caudal end of the plug-like closure device comprises a closure section.

41. The fistula blocker of claim 38, wherein the plug-like closure device has a conical shape.

42. The fistula blocker of claim 38, wherein the plug-like closure device has a concave outer shape.

43. The fistula blocker of claim 38, wherein the plug-like closure device has an egg shape.

44. The fistula blocker of claim 38, wherein the length of the plug-like closure device is about 2 cm.

45. The fistula blocker of claim 38, wherein the plug-like closure device is hollow.

46. The fistula blocker of claim 38, wherein the plug-like closure device comprises a plurality of channels disposed therein.

47. The fistula blocker of claim 38, wherein the plug-like closure device comprises a plurality of indentations on the surface thereof.

48. The fistula blocker of claim 38, wherein the plug-like closure device further comprises an anchoring device.

49. The fistula blocker of claim 48, wherein the anchoring device comprises a plurality of barbed sections.

50. The fistula blocker of claim 49, wherein the plurality of barbed sections are restricted in their flexibility.

51. The fistula blocker of claim 38, wherein the length of the plug-like closure device is 0.5 to 1 cm.

52. The fistula blocker of claim 38 wherein the plug-like closure device comprises titanium.

* * * * *